(12) United States Patent
Fraissignes et al.

(10) Patent No.: US 7,445,925 B2
(45) Date of Patent: Nov. 4, 2008

(54) AEQUORIN AS A REPORTER GENE IN YEAST

(75) Inventors: Pauline Fraissignes, Marseille (FR); Denis Guedin, Montauroux (FR)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 55 days.

(21) Appl. No.: 10/280,911

(22) Filed: Oct. 25, 2002

(65) Prior Publication Data

US 2003/0157640 A1   Aug. 21, 2003

Related U.S. Application Data

(60) Provisional application No. 60/346,022, filed on Jan. 4, 2002.

(30) Foreign Application Priority Data

Oct. 27, 2001   (EP)   ................................ 01125709

(51) Int. Cl.
  *C12N 1/19*   (2006.01)
  *C07H 21/04*   (2006.01)
(52) U.S. Cl. .................. 435/254.2; 536/23.5
(58) Field of Classification Search ................ 536/23.1; 325/254.2
  See application file for complete search history.

(56) References Cited

U.S. PATENT DOCUMENTS

| | | | | |
|---|---|---|---|---|
| 4,816,567 A | * | 3/1989 | Cabilly et al. | 530/387.3 |
| 5,846,819 A | * | 12/1998 | Pausch et al. | 435/320.1 |
| 5,876,951 A | | 3/1999 | Fowlkes et al. | |

OTHER PUBLICATIONS

Marchese et al., Genomics (1995), vol. 29: pp.335-344.*
Batiza et al., JBC (1996), vol. 271(38): pp. 23357-23362, esp. p. 23357.*
Inouye et al. (1994), Accession #: L29571.*
Kendall et al., Trends Biotech. (1998), vol. 16(5): pp. 216-224, esp. p. 219.*
Brini et al. JBC (1995), vol. 270(17): pp. 9896-9903, esp. pp. 9899-9901.*
Janoo et al., Genetics 2001, vol. 157(3): pp. 1205-1215.*
Ren et al. 2000. Science. 290: 2306-2309.*
Price et al, 1996, Molecular Pharmacology, 50: 829-837.*
Dowell et al, 2002. Receptors and Channels. 8: 343-352.*
Ladd et al, Trends in Biotechnology. 23(7) 367-373).*
Tanahashi et al, 1990. Gene. 96(2): 249-255.*
Brini Marisa et al., Targeted Recombinant Aequorins: Tools For Monitoring [Ca2+] In The Various Compartments Of A Living Cell, Microscopy Research And Technique (1999) 46 pp. 380-389.
Hadcock John R. et al., Ligand Screening Of G Protein-Coupled Receptors in Yeast, CRC Press, LLC (2000) pp. 49-66.
Hagen David C. et al., Pheromone Response Elements Are Necessary And Sufficient For Basal And Pheromone-Induced Transcription Of the FUS1 Gene Of Saccharomyces Cerevisiae, Molecular And Cellular Biology (1991) 11 pp. 2952-2961.

(Continued)

*Primary Examiner*—Elizabeth C. Kemmerer
*Assistant Examiner*—Zachary C Howard

(57) ABSTRACT

A yeast transduction pathway-inducible expression cassette for aequorin and yeast cells containing the expression cassette are disclosed, as well as methods of using the yeast cells in screening assays.

3 Claims, 7 Drawing Sheets

OTHER PUBLICATIONS

Iida Hidetoshi et al., Essential Role For Induced Ca2+ Influx Followed By [Ca2+] Rise In Maintaining Viability Of Yeast Cells Late In The Mating Pheromone Response Pathway, The Journal Of Biological Chemistry (1990) 265 pp. 13391-13399.

Inouye Satoshi et al., Overexpression And Purificaiton Of The Recombinant Ca2+ Binding Protein, Apoeaquorin, J Biochem (1989) 105 pp. 473-477.

Ito Hisao et al., Transformation Of Intact Yeast Cells Treated With Alkali Cations, Journal Of Bacteriology (1983) 153 pp. 163-168.

Johnson Frank H. et al., Introduction To The Bioluminescence Of Medusae, With Special Reference To The Photoprotein Aequorin, Methods In Enzymology (1978) 57 pp. 271-291.

King Klim et al., Control Of Yeast Mating Signal Transduction By A Mammalian B2-Adrenergic Receptor And Gs Subunit, Erratum Appears In Science (1990) 250 pp. 121-123.

Leberer Ekkehard et al., Pheromone Signalling And Polarized Morphogenesis In Yeast, Current Opinion In Genetics & Development (1997) 7 pp. 59-66.

Miller Andrew L. et al., Imaging [Ca2+] With Aequorin Using A Photon Imaging Detector, Methods In Cell Biology (1994) 40 pp. 305-0338.

Nakajima-Shimada Junko et al., Ca2+Signal Is Generated Only Once In The Mating Pheromone Response Pathway In Saccharomyces Cerevisiae, Cell Structure And Function (2000) 25 pp. 125-131.

Nakajima-Shimada Junko et al., Galactose-Dependent Expression Of THe Recombinant Ca2+ Binding Photoprotein Aequorin In Yeast, Biochemical And Biophysical Research Communications (1991) 174 pp. 115-122.

Nakajima-Shimada Junko et al., Monitoring Of Intracellular Calcium In Saccharomyces Cerevisiae With An Apoaequorin cDNA Expression System, Proc. Nat'l. Acad Sci. USA (1991) 88 pp. 6878-6882.

Ohmiya Yoshihiro et al., Shining The Light: The Mechanism Of The Bioluminescence Reaction Of Calcium-Binding Photoproteins, Chemistry & Biology (1996) 3 pp. 337-347.

Rizzuto Rosario et al., Rapid Changes Of Mitochondrial Ca2+ Revealed By Specifically Targeted Recombinant Aequorin, Erratum Appears In Nature (1992) 358 pp. 325-327.

Sheu Yeong-An et al., Measurement Of Intracellular Calcium Using Bioluminescent Aequorin Expressed In Human Cells, Analytical Biochemistry (1993) 209 pp. 343-347.

Shimomura Osamu et al., Peroxidized Coelenterazine, The Active Group In The Photoprotein Aequorin, Proc. Nat'l Acad. Sci. USA (1978) 75 pp. 2611-2615.

Stables Jenny et al., Recombinant Aequorin As Reporter Of Changes Intracellular Calcium In Mammalian Cells, Method In Enzymology (2000) 327 pp. 456-471.

Thomas Andrew P. et al., The Use Of Fluorescent Indicators For Measurements Of Cytosolic-Free Calcium Concentration In Cell Populations And Single Cells, A Pratical Approach (1991) pp. 1-54.

Julie A. Pitcher et al., G Protein-coupled Receptor Kinases, Annu. Rev. Biochem, 1998, vol. 67, pp. 653-692.

N. Dhanasekaran et al., G Protein-coupled Receptor Systems Involved in Cell Growth and Oncogenesis, Endocrine Reviews, vol. 16, No. 3, 1995, pp. 259-270.

S.J. Hill et al., Reporter-gene systems for the study of G-protein-coupled receptors, Current Opinion in Pharmacology, 2001, vol. 1, pp. 526-532.

* cited by examiner

FIG. 1

```
                                          HindIII
                                          ~~~~~~~
    1   ATGACAAGCA AACAATACTC AGTCAAGCTT ACATCAGACT TCGACAACCC
        TACTGTTCGT TTGTTATGAG TCAGTTCGAA TGTAGTCTGA AGCTGTTGGG
   51   AAGATGGATT GGACGACACA AGCATATGTT CAATTTCCTT GATGTCAACC
        TTCTACCTAA CCTGCTGTGT TCGTATACAA GTTAAGGAA CTACAGTTGG
  101   ACAATGGAAA AATCTCTCTT GACGAGATGG TCTACAAGGC ATCTGATATT
        TGTTACCTTT TTAGAGAGAA CTGCTCTACC AGATGTTCCG TAGACTATAA
  151   GTCATCAATA ACCTTGGAGC AACACCTGAG CAAGCCAAAC GACACAAAGA
        CAGTAGTTAT TGGAACCTCG TTGTGGACTC GTTCGGTTTG CTGTGTTTCT
  201   TGCTGTAGAA GCCTTCTTCG GAGGAGCTGG AATGAAATAT GGTGTGGAAA
        ACGACATCTT CGGAAGAAGC CTCCTCGACC TTACTTTATA CCACACCTTT
  251   CTGATTGGCC TGCATATATT GAAGGATGGA AAAAATTGGC TACTGATGAA
        GACTAACCGG ACGTATATAA CTTCCTACCT TTTTTAACCG ATGACTACTT
  301   TTGGAGAAAT ACGCCAAAAA CGAACCAACG CTCATCCGTA TATGGGGTGA
        AACCTCTTTA TGCGGTTTTT GCTTGGTTGC GAGTAGGCAT ATACCCCACT
                             EcoRV
                             ~~~~~~
  351   TGCTTTGTTT GATATCGTTG ACAAAGATCA AAATGGAGCC ATTACACTGG
        ACGAAACAAA CTATAGCAAC TGTTTCTAGT TTTACCTCGG TAATGTGACC
  401   ATGAATGGAA AGCATACACC AAAGCTGCTG GTATCATCCA ATCATCAGAA
        TACTTACCTT TCGTATGTGG TTTCGACGAC CATAGTAGGT TAGTAGTCTT
  451   GATTGCGAGG AAACATTCAG AGTGTGCGAT ATTGATGAAA GTGGACAACT
        CTAACGCTCC TTTGTAAGTC TCACACGCTA TAACTACTTT CACCTGTTGA
                                                          NcoI
                                                          ~~~~~~
                                                          BamHI
                                                          ~~
  501   CGATGTTGAT GAGATGACAA GACAACATTT AGGATTTTGG TACACCATGG
        GCTACAACTA CTCTACTGTT CTGTTGTAAA TCCTAAAACC ATGTGGTACC
        BamHI
        ~~~~
  551   ATCCTGCTTG CGAAAAGCTC TACGGTGGAG CTGTCCCCTA A
        TAGGACGAAC GCTTTTCGAG ATGCCACCTC GACAGGGGAT T
```

FIG. 2

HindIII
      ~~~~~~
    1 AAGCTTGGAT CGCCCTTTTT GACGTATTGA ATGGCATAAT TGCACTGTCA
      TTCGAACCTA GCGGGAAAAA CTGCATAACT TACCGTATTA ACGTGACAGT
   51 CTTTTCGCGC TGTCTCATTT TGGTGCGATG ATGAAACAAA CATGAAACGT
      GAAAAGCGCG ACAGAGTAAA ACCACGCTAC TACTTTGTTT GTACTTTGCA
  101 CTGTAATTTG AAACAAATAA CGTAATTCTC GGGATTGGTT TTATTTAAAT
      GACATTAAAC TTTGTTTATT GCATTAAGAG CCCTAACCAA AATAAATTTA
  151 GACAATGTAA GAGTGGCTTT GTAAGGTATG TGTTGCTCTT AAAATATTTG
      CTGTTACATT CTCACCGAAA CATTCCATAC ACAACGAGAA TTTTATAAAC
  201 GATACGACAT CCTTTATCTT TTTTCCTTTA AGAGCAGGAT ATAAGCCATC
      CTATGCTGTA GGAAATAGAA AAAAGGAAAT TCTCGTCCTA TATTCGGTAG
                             NcoI
                           ~~~~~~~~
  251 AAGTTTCTGA AAATCACCAT GGGAATTC
      TTCAAAGACT TTTAGTGGTA CCCTTAAG raw data

| stimulation time | 3 hours | | | | | 6 hours | | | | | 24 hours | | | | |
|---|---|---|---|---|---|---|---|---|---|---|---|---|---|---|---|
| [α-factor] | | | | mean | stand dev | | | | mean | stand dev | | | | mean | stand dev |
| 0 | 47 | 20 | 39 | 22 | 23 | 131 | 142 | 155 | 99 | 66 | 145 | 135 | 97 | 115 | 43 |
| 0,01 nM | 52 | 75 | 71 | 63 | 16 | 209 | 232 | 259 | 152 | 118 | 199 | 138 | 163 | 152 | 42 |
| 1 nM | 99 | 104 | 137 | 102 | 3 | 1276 | 1280 | 1250 | 853 | 736 | 433 | 617 | 302 | 595 | 153 |
| 100 nM | 165 | 198 | 310 | 182 | 24 | 1457 | 899 | 770 | 793 | 723 | 1990 | 2169 | 1982 | 1627 | 789 | ratio

| stimulation time | 3 hours | | | | | 6 hours | | | | | 24 hours | | | | |
|---|---|---|---|---|---|---|---|---|---|---|---|---|---|---|---|
| [α-factor] | | | | mean | stand dev | | | | mean | stand dev | | | | mean | stand dev |
| 0 | 1 | 1 | 1 | 1 | 1 | 1 | 1 | 1 | 1 | 0 | 1 | 1 | 1 | 1 | 0 |
| 0,01 nM | 1 | 4 | 2 | 2 | 2 | 2 | 2 | 2 | 2 | 0 | 1 | 1 | 2 | 1 | 1 |
| 1 nM | 2 | 5 | 4 | 4 | 2 | 10 | 9 | 8 | 7 | 4 | 3 | 5 | 3 | 4 | 1 |
| 100 nM | 4 | 10 | 8 | 7 | 4 | 11 | 6 | 5 | 7 | 3 | 14 | 16 | 20 | 11 | 7 |

AEQUORIN AS A REPORTER GENE IN YEAST

FIELD OF THE INVENTION

The present invention relates to a modified yeast cell containing Aequorin as a reporter gene for detection of signaling pathway activity and to methods of using such modified yeast cells.

BACKGROUND OF THE INVENTION

Aequorin is a photoprotein isolated from luminescent jellyfish Aequoria victoria.

Apoaequorin is a protoprotein which, upon binding to coelenterazine, can emit photons in the presence $Ca^{2+}$. The Aequorin complex comprises a 22,514 MW Apoaequorin protein (SEQ ID NO. 2), molecular oxygen and the luminophore coelenterazine (Inouye et al., 1989;Johnson and Shimomura, 1978;Shimomura and Johnson, 1978). When three $Ca^{2+}$ ions bind to this complex, coelenterazine is oxidized to coelenteramide, with a concomitant release of carbon dioxide and blue light (emission maximum ~466 nm) (FIG. 7).

Because of its $Ca^{2+}$-dependent luminescence, the Aequorin complex has been extensively used as an intracellular $Ca^{2+}$ indicator detected by chemiluminescence assay.

Aequorin reportedly does not disrupt cell functions or embryo development (Miller et al., 1994).

Aequorin can be easily expressed in mammalian cells. It has been utilized to monitor the cytosolic-free calcium concentration (Thomas and Delaville, 1991) (Sheu et al., 1993) (Stables et al., 2000).

Aequorin can also be easily targeted to specific organelles such as mitochondria (Brini et al., 1999) (Rizzuto et al., 1992) to monitor different aspects of calcium homeostasis.

The pharmaceutical industry has taken wide advantage of the different properties of Aequorin, particularly in High Throughput Screens (Detheux, 2000). The activation of a receptor coupled to the phospholipase C transduction pathway can be easily detected in presence of the photoprotein Aequorin, because of an instantaneous release of calcium from the endoplasmic reticulum. WO0002045, Detheux et al. (EUROSCREEN S.A.) describes a high-throughput screening diagnostic and/or dosage method of an agonist and/or an antagonist for a calcium-coupled receptor (in mammalian cells) where Aequorin is used as marker for intracellular calcium changes upon receptor stimulation.

It has been previously shown that Aequorin can be functionally expressed in yeast and detected. Nakajima-Shimada et al. (Nakajima-Shimada et al., 1991b) describe the monitoring of intracellular calcium in *Saccharomyces cerevisiae* with an Apoaequorin cDNA expression system. Here, Aequorin was again used as a marker of intracellular calcium upon stress or glucose variations in the medium.

In contrast to mammalian signal transduction, there is no comparable $Ca^{2+}$ release from the endoplasmic reticulum upon G protein-coupled receptor (GPCR) activation in yeast cells. The addition of α-factor to a yeast cell (i.e. stimulation of the GPCR Ste2) raises $[Ca^{2+}]i$ from a basal level of approximately 100 nM to a few hundred nanomolar in the cells, simultaneously with the induction of $Ca^{2+}$ influx. When the cells are incubated with α-factor in a $Ca^{2+}$-deficient medium, $Ca^{2+}$ influx is greatly reduced, and the rise in $[Ca^{2+}]i$ is not detected (Iida et al., 1990). This slight variation in cytosolic $[Ca^{2+}]$ does not interfere with pathway activity detection according to the instant invention.

A limited number of reporter genes are known for use in the yeast cells, such as *Saccharomyces cerevisiae*, and their use is not always appropriate in screening methods. Accordingly, there is a continuing need for additional yeast reporter gene systems optimized for screening methods.

For screening purposes, a reporter gene product must be easy to detect. Accordingly, the most commonly utilized reporter gene in yeast is LacZ, which encodes the very big and stable enzyme β-Galactosidase, which is detected in a chemiluminescence assay. However, bacterial contamination may occur in yeast cultures during assays and most of the contaminants physiologically express a β-Galactosidase activity. Contaminated cultures give a very strong signal in the presence of β-Galactosidase substrates, leading to false positives in an assay.

SUMMARY OF THE INVENTION

A yeast cell is provided, containing an aequorin-encoding deoxyribonucleic acid sequence expressibly linked to a promoter, wherein the promoter is responsive to activation of a transduction pathway. By describing a promoter as "responsive to activation of a transduction pathway", the applicants intend that expression from the promoter is either upregulated or downregulated by the activation of the transduction pathway.

The invention also provides an isolated deoxyribonucleic acid sequence of an aequorin encoding sequence expressibly linked to a promoter responsive to activation of a yeast transduction pathway.

In addition, the invention provides a method for identifying compounds that modulate heterologous cell surface protein-mediated aequorin expression, the method comprising:
  (a) providing a yeast cell comprising an aequorin-encoding deoxyribonucleic acid sequence expressibly linked to a first, transduction pathway-activated, promoter and a heterologous cell surface protein-encoding deoxyribonucleic acid expressibly linked to a second promoter, wherein the heterologous cell surface protein is an element of the transduction pathway;
  (b) incubating the yeast cell with a compound; and
  (c) determining an amount of aequorin expression by the incubated yeast cell.

By describing a protein as an "element of the transduction pathway", applicants intend that the protein, alone or in combination with other factors, is capable of specifically activating or inactivating the transduction pathway.

BRIEF DESCRIPTION OF THE DRAWINGS

FIG. 1: Aequorin—open reading frame (SEQ ID NO. 1)
FIG. 2: 4PRE sequence (SEQ ID NO. 3)

DETAILED DESCRIPTION OF THE INVENTION

Figure 3:
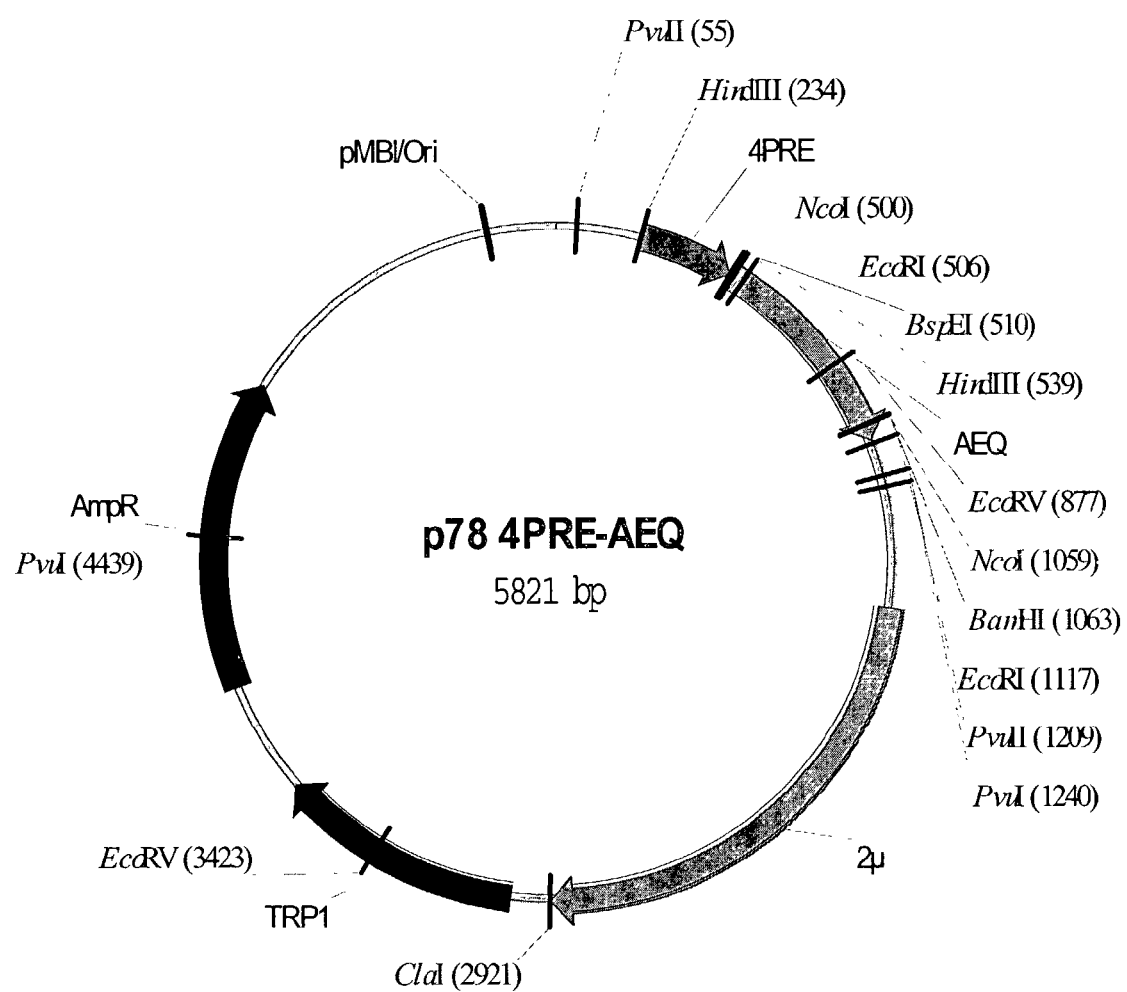
FIG. 3: Restriction map of p78 4PRE-Aeq

Aequorin is a photoprotein detected, like β-Galactosidase, in a chemiluminescence assay. As Aequorin (22514 MW) is five times smaller than β-Galactosidase (116351 MW), it can accumulate in a greater amount to give a higher sensitivity to the assay and report better up- and down-regulations of the pathway (activating or inhibiting effect of the tested compound). In summary, Aequorin is more suitable than β-Galactosidase for use in sensitive assays.

Aequorin can be expressed functionally by the yeast *S. cerevisiae* (Nakajima-Shimada et al., 1991a).

Aequorin is easily detected in a luminescent assay, in the presence of coelenterazin and Ca2+.

So far, Aequorin has not been utilized as a pathway activity reporter gene in yeast (as opposed to other reporter genes such as LacZ and HIS3, which have been used with a mammalian G protein coupled receptor coupled to the yeast pheromone pathway (King et al., 1990;Hadcock and Pausch, 1999)).

The control of yeast mating signal transduction by a mammalian receptor ($\beta_2$-adrenergic) was first described in 1990 (King et al.,1990). U.S. Pat. No. 5,876,951A claims yeast cells engineered to produce pheromone system protein surrogates and uses therefor (pFUS1-lacZ and pFUS1-Luciferase).

Aequorin is used as a transduction pathway dependent reporter: the Aequorin reporter gene is then expressed only in case of activation of the transduction pathway of interest. For instance, to measure the activity of the pheromone responsive pathway, the expression of the reporter gene Aequorin is controlled by a promoter containing some Pheromone Responsive Elements. The FUS1 promoter is the most commonly utilized. In haploid *Saccharomyces cerevisiae* cells, GPCRs regulate the mating process. The receptor Ste2 detects the presence of cells of the opposite mating type (through binding of peptide mating pheromones), and activates intracellular heterotrimeric G proteins, thus initiating the mating process. Gpa1 (α subunit) dissociates from the βγ (Ste4-Ste18) complex which activates downstream elements of the pheromone response pathway which includes a well-characterized mitogen-activated protein kinase (MAP kinase) cascade. The activated transcription factor Ste12 can then initiate the transcription of several mating factor-inducible genes such as FUS1.

Controlled by a pheromone dependent gene promoter, Aequorin is expressed proportionally to the activation of the yeast pheromone transduction pathway. Aequorin detection signal quantifies the activity of the pathway.

Pheromone response elements are necessary and sufficient for basal and pheromone-induced transcription of the FUS1 gene of *Saccharomyces cerevisiae* (Hagen et al., 1991).

The present invention relates to a modified yeast cell comprising an Aequorin encoding sequence under the control of a promoter of a mating factor-inducible gene, the FUS1 promoter or a part thereof, e.g. 4PRE. In a special embodiment of the invention the Aequorin encoding sequence is SEQ ID NO. 1. In another special embodiment of the invention to modified yeast cell expresses another heterologous protein, preferably a heterologous protein to be investigated. Examples for such other heterologous proteins are cell surface proteins, e.g. G protein coupled receptors or kinases. Yeast cells which can be modified are for example *Saccharomyces cerevisiae*, *Schizosaccharomyces pombe* and *Candida albicans*.

The present invention also relates to the use of the modified yeast cells, e.g. for screening of compounds.

The present invention relates to a method for identifying compounds that modulate heterologous cell surface protein-mediated aequorin expression, the method involving the steps of:

(a) providing a yeast cell comprising an aequorin-encoding deoxyribonucleic acid sequence expressibly linked to a first, transduction pathway-activated, promoter and a heterologous cell surface protein-encoding deoxyribonucleic acid expressibly linked to a second promoter, wherein the heterologous cell surface protein is an element of the transduction pathway;

(b) incubating the yeast cell with a compound; and (c) determining an amount of aequorin expression by the incubated yeast cell.

In a particular embodiment, the transduction pathway-activated promoter is a mating factor-inducible, such as a pheromone responsive element. In another particular embodiment, the heterologous cell surface protein is a G protein coupled receptor or a kinase.

Our observations show that Aequorin is superior to β-Galactosidase in a transduction pathway dependent reporter assay.

EXAMPLES

Example 1

Materials and Methods

As a yeast strain W303 MAT a, far::hisG, sst2::URA3$^{FOA}$, fus1::HIS3 was used.

The yeast strain was transformed with the different plasmids according to the Lithium acetate method (Ito et al., 1983)).

Example 2

Construction of the Aequorin expression vectors

The full length cDNA Aequorin gene was amplified by PCR using the chimerical mitochondrial Aequorin mtAEQ (where the truncated N-terminus is fused to the human cytochrome C targeting signal (Rizzuto et al., 1992)) as a template. The 5' PCR primer contained the 50 first nucleotides of aequorin wild type sequence and an EcoRI (noted in bold type below) cloning site. The 3' primer did not contain any cloning site.

```
5' AQWT:                            (SEQ ID NO. 4)
5'-CCG GAA TTC CGG ATG ACA AGC AAA CAA TAC TCA GTC
AAG CTT ACA TCA GAC TTC GAC AAC CC.

3' AQWT:                            (SEQ ID NO. 5)
5'-GGG CCT TAG GGG ACA GCT CCA CCG TAG AGC.
```

The full-length wild type Aequorin coding sequence (FIG. 1) was then cloned in the pheromone pathway activity dependent expression vector p78-4PRE (TRP1, 2μ) (FIG. 3).

The minimal and sufficient portion of the FUS1 promoter (Hagen et al., 1991) that we called 4PRE is consisting of the last 261 bp of the promoter region, upstream of the FUS1 open reading frame. This promoter was amplified from wild-type yeast genomic DNA with the two following primers:

```
261 sens Fus:                       (SEQ ID NO. 6)
5'-CTA AAG CTT GGA TCG CCC TTT TTG ACG TAT TGA 1 Fus rev:                          (SEQ ID NO. 7)
5'-A GA ATT CCC ATG GTG ATT TTC AGA AAC TTG ATG
GCT T.
```

Example 3

Construction of the β-Galactosidase expression vectors

To allow the comparison, LacZ was sub-cloned in the same way than aequorin, into the same expression vector and without any fusion with the 5' sequence of a endogenous gene (as is was often done to increase the expression level (King et al., 1990))).

Figure 4:
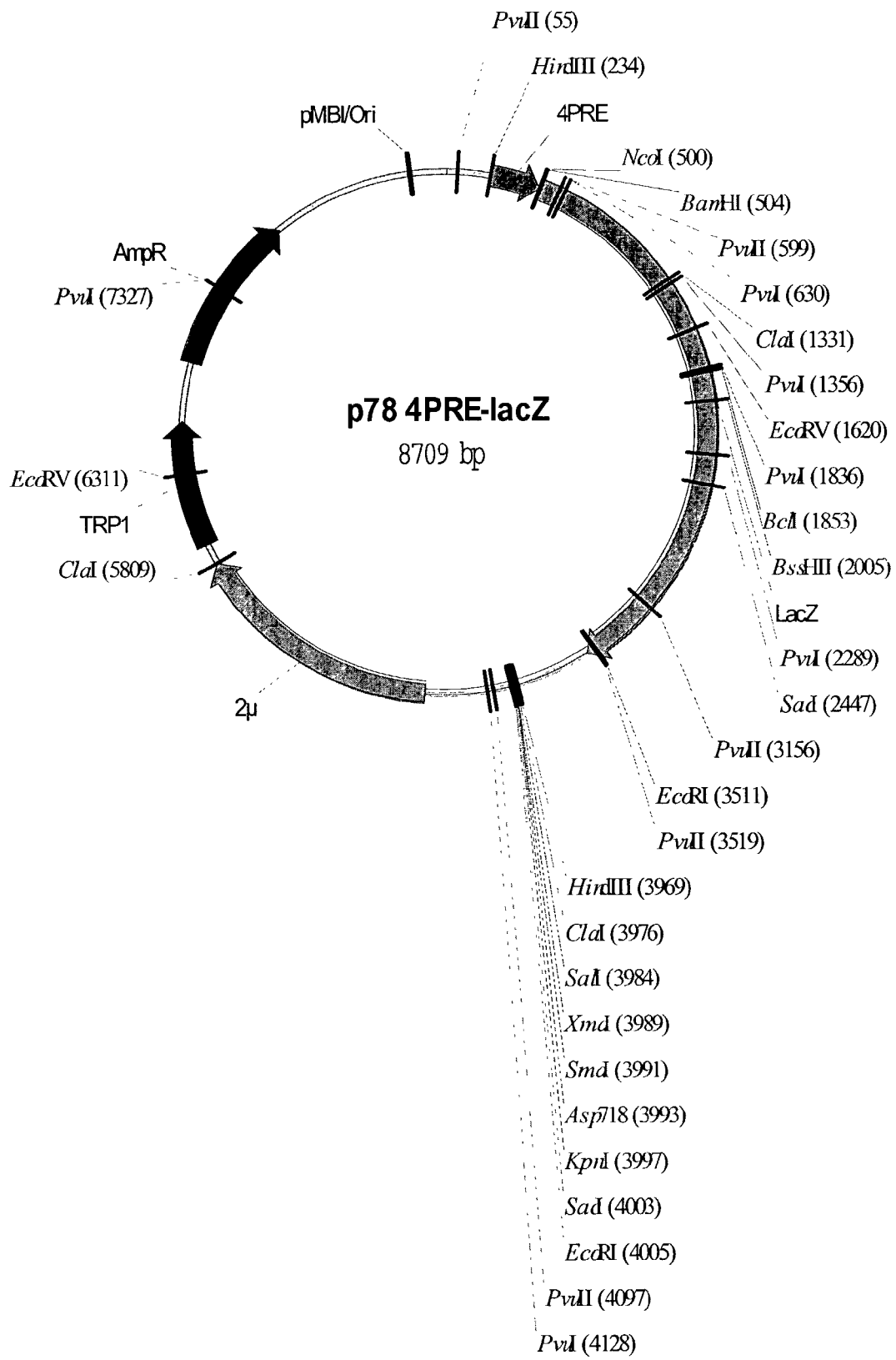
FIG. 4: Restriction map of p78 4PRE-lacZ

The full-length *Escherichia coli* β-Galactosidase gene sequence was cloned in the pheromone pathway activity dependent expression vector p78-4PRE (TRP1, 2μ) (FIG. 4).

Example 4

Aequorin detection

The cells are distributed and/or grown in a white 96-well plate, in a volume of 100 μl.

30 minutes before the measurement time point, 10 μl of a 5 μM coelenterazine (Molecular Probes) solution is distributed in each well (to obtain a 0.5 μM final concentration) to load the cells.

The plate is then incubated at 30° C. for the last 30 minutes.

Aequorin detection is made in a luminometer with injecting system (Luminoskan, Labsystems). For each well, immediately after injection of a 10 mM CaCl2 solution (1 M CaCl2 diluted in lysis buffer Y-PER from Pierce), the luminescent signal is integrated for 15 seconds.

To avoid the intermediate step of loading, it is possible to introduce coelenterazine in the medium at the beginning of the assay: coelenterazine is added at a concentration of 0.5 μM.

Example 5

β-Galactosidase detection

The cells are distributed and/or grown in a white 96-well plate, in a volume of 100 μl. At the measurement time point, each well receives 100 μl of a β-Galactosidase detection mix (Gal-screen, Tropix).

The plate is incubated for one hour at 28° C.

β-Galactosidase signal is read in a luminometer; the luminescent signal is integrated for 0.5 seconds.

Example 6

Classical reporter of a pathway activity

In this assay, the expression of the two reporter genes depends on the activity of the pheromone mating pathway (Leberer et al., 1997). The minimal promoter 4PRE amplified from the FUS1 promoter region (Hagen et al., 1991) is activated only in case of a mating signal. This signal is elicited by stimulation of the pheromone receptor Ste2 by its ligand α-factor.

Three colonies of the yeast strain transformed with either p78 4PRE-AEQ or p78 4PRE-LacZ plasmids were grown in the appropiate medium (SC Glucose—Trp) to stationary phase and then diluted in the same medium (with 0.5 μM coelenterazin for the aequorin strain) containing 0; $10^{-7}$; $10^{-9}$; $10^{-11}$M α-factor (Sigma). The plates were then shaken at 30° C., 700 r.p.m., for 3, 6 and 24 hours.

Figure 5:
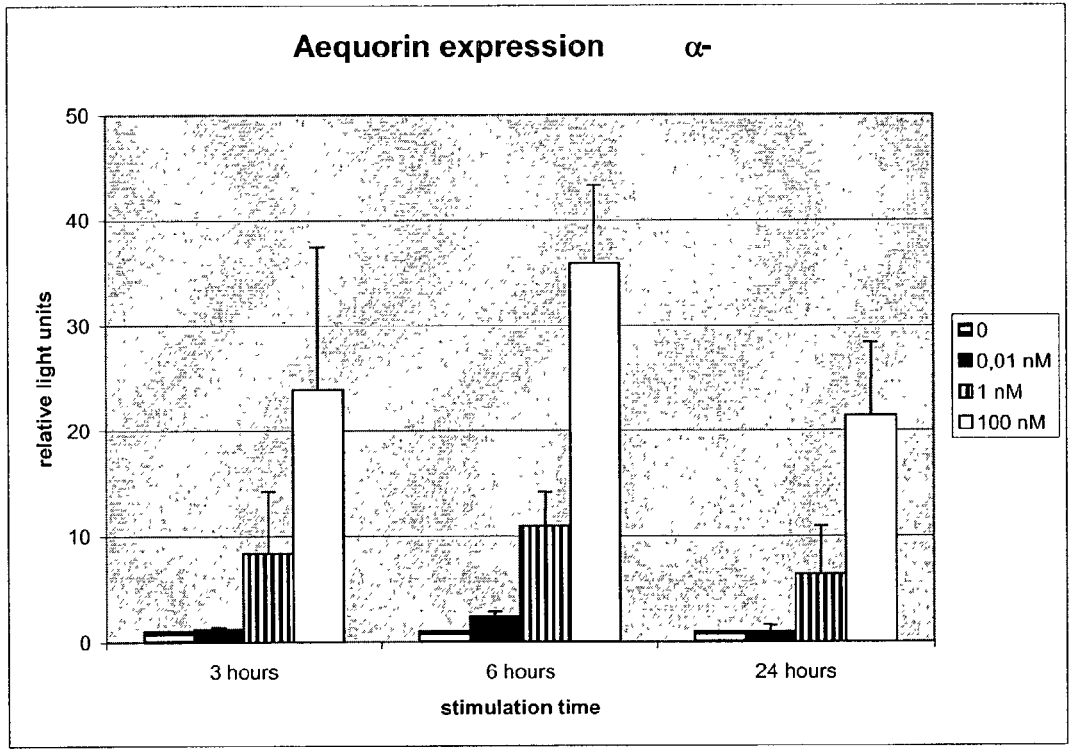
FIG. 5: Results of pathway activity reporter/Aequorin activity
Figure 6:
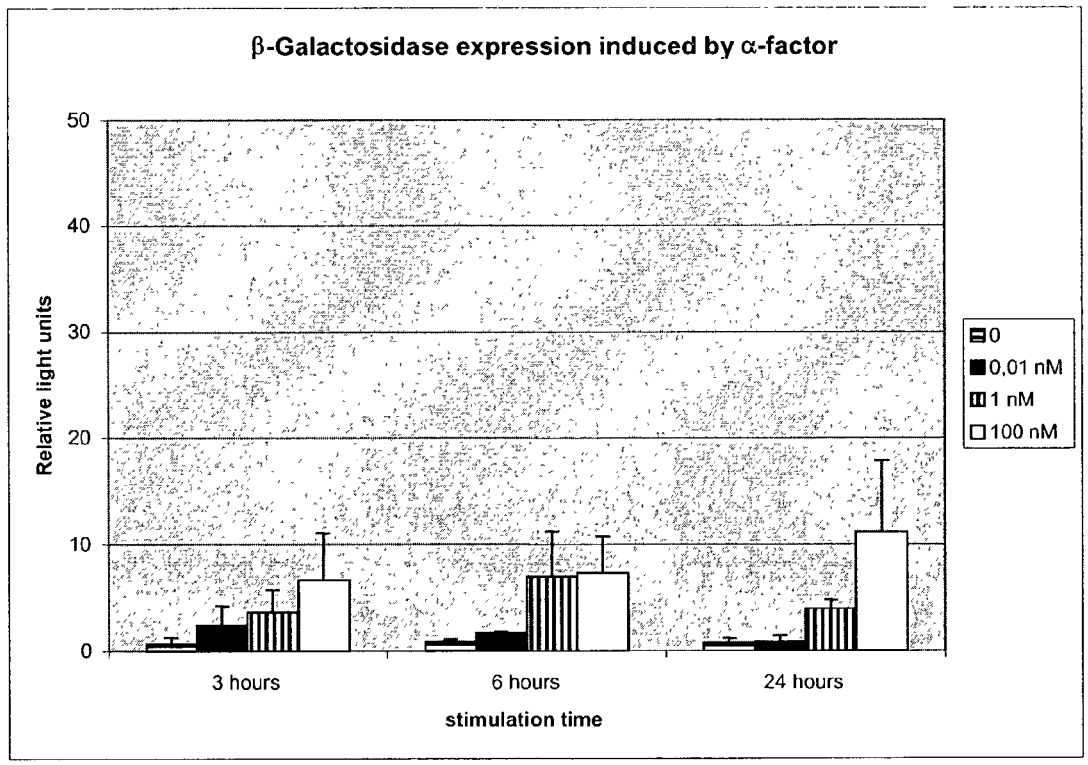
FIG. 6: Results of pathway activity reporter/β-Galactosidase activity
Figure 7:
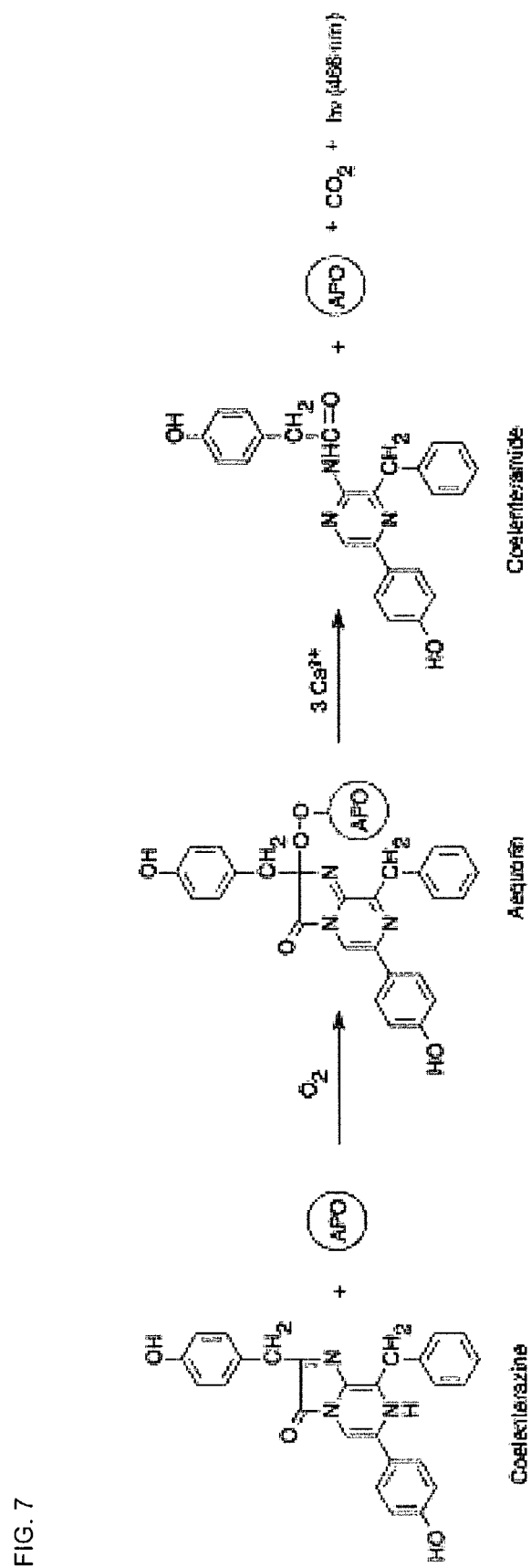
FIG. 7: $Ca^{2+}$-dependent generation of luminescence by the aequorin complex, which contains apoaequorin (APO) and coelenterazine (Ohmiya and Hirano, 1996)).

To allow the comparison between the two reporters and the different stimulation times, the measured detection numbers of Aequorin (FIG. 5) and β-Galactosidase (FIG. 6) are expressed as a ratio: stimulated/non stimulated.

After 3 hours of stimulation, the detected ratio is already higher for Aequorin than for β-Galactosidase with 1 nM or 100 nM α-factor (ratio respectively of 8 and 24 with Aequorin, 4 and 7 with β-Galactosidase). After 6 hours of stimulation, the β-Galactosidase ratio stays at the same level (ratio of 7 for both α-factor concentrations) but Aequorin detection shows higher levels (ratio of 11 with 1 nM α-factor and 36 with 100 nM α-factor). After 24 hours stimulation, Aequorin numbers stay higher than β-Galactosidase.

All together, this experiment shows that Aequorin reflects better than β-Galactosidase the stimulation of Ste2 with different concentrations of ligand, among a large time frame.

REFERENCE LIST

Brini M, Pinton P, Pozzan T and Rizzuto R (1999) Targeted Recombinant Aequorins: Tools for Monitoring [Ca$^{2+}$] in the Various Compartments of a Living Cell. Microsc Res Tech 46: pp 380-389.

Detheux M (2000) Orphan Receptors: the Quest for New Drug Targets. Innovations in Pharmaceutical Technology 00: pp 27-34.

Hadcock J R and Pausch M (1999) Ligand screening of G protein-coupled receptors in yeast, in G Protein-Coupled Receptors (Haga T and Berstein G eds) pp 49-69, CRC Press LLC, Boca Raton, Fla.

Hagen D C, McCaffrey G and Sprague G F J (1991) Pheromone Response Elements Are Necessary and Sufficient for Basal and Pheromone-induced Transcription of the FUS1 Gene of Saccharomyces Cerevisiae. Mol Cell Biol 11: pp 2952-2961.

Iida H, Yagawa Y and Anraku Y (1990) Essential Role for Induced Ca2+ Influx Followed by [Ca2+]i Rise in Maintaining Viability of Yeast Cells Late in the Mating Pheromone Response Pathway. A Study of [Ca2+]i in Single *Saccharomyces Cerevisiae* Cells With Imaging of Fura-2. J Biol Chem 265: pp 13391-13399.

Inouye S, Aoyama S, Miyata T, Tsuji F I and Sakaki Y (1989) Overexpression and Purification of the Recombinant Ca$^{2+}$-Binding Protein, Apoaequorin. J Biochem (Tokyo) 105: pp 473-477.

Ito H, Fukuda Y, Murata K and Kimura A (1983) Transformation of Intact Yeast Cells Treated With Alkali Cations. J Bacteriol 153: pp 163-168.

Johnson F H and Shimomura O (1978) Bioluminescence and Chemiluminescence: Introduction to the Bioluminescence of Medusae, With Special Reference to the Photoprotein Aequorin. Methods Enzymol 57: pp 1-653.

King K, Dohiman H G, Thorner J, Caron M G and Lefkowitz R J (1990) Control of Yeast Mating Signal Transduction by a Mammalian B$_2$-Adrenergic Receptor and Gs Alpha Subunit [Published Erratum Appears in Science Jan. 11, 1991; 251(4990):144]. Science 250: pp 121-123.

Leberer E, Thomas D Y and Whiteway M (1997) Pheromone Signalling and Polarized Morphogenesis in Yeast. Curr Opin Genet Dev 7: pp 59-66.

Miller A L, Karplus E and Jaffe L F (1994) Imaging [Ca$^{2+}$]i With Aequorin Using a Photon Imaging Detector. Methods Cell Biol 40: pp 305-338.

Nakajima-Shimada J, Iida H, Tsuji F I and Anraku Y (1991a) Galactose-Dependent Expression of the Recombinant Ca2 (+)-Binding Photoprotein Aequorin in Yeast. Biochem Biophys Res Commun 174: pp 115-122.

Nakajima-Shimada J, Iida H, Tsuji F I and Anraku Y (1991b) Monitoring of Intracellular Calcium in *Saccharomyces*

Cerevisiae With an Apoaequorin CDNA Expression System. Proc Natl Acad Sci USA 88: pp 6878-6882.
Ohmiya Y and Hirano T (1996) Shining the Light: the Mechanism of the Bioluminescence Reaction of Calcium-Binding Photoproteins. Chem Biol 3: pp 337-347.
Rizzuto R, Simpson A W, Brini M and Pozzan T (1992) Rapid Changes of Mitochondrial Ca2+ Revealed by Specifically Targeted Recombinant Aequorin [Published Erratum Appears in Nature 1992 Dec. 24-31;360(6406):768].Nature 358: pp 325-327.
Sheu Y A, Kricka L J and Pritchett D B (1993) Measurement of Intracellular Calcium Using Bioluminescent Aequorin Expressed in Human Cells. Anal Biochem 209: pp 343-347.

Shimomura O and Johnson F H (1978) Peroxidized Coelenterazine, the Active Group in the Photoprotein Aequorin. Proc Natl Acad Sci USA 75: pp 2611-2615.
Stables J, Maftheakis L C, Chang R and Rees S (2000) Recombinant Aequorin As Reporter of Changes in Intracellular Calcium in Mammalian Cells. Methods Enzymol 327: pp 456-471.
Thomas A P and Delaville F (1991) The Use of Fluorescent Indicators for measurements of cytosolic-free calcium concentration in cell populations and single cells., in Cellular Calcium: A Practical Approach (McCormack J G and Cobbold P H eds) pp 1-54.

The invention claimed is:

1. A yeast cell comprising an aequorin-encoding deoxyribonucleic acid (DNA) sequence expressibly linked to a first promoter, wherein the first promoter is responsive to activation by the pheromone responsive pathway and is made by a process comprising amplifying the first promoter from wild-type yeast genomic DNA using two primers, one comprising SEQ ID NO: 6 and one comprising SEQ ID NO: 7, the yeast cell further comprising a G protein coupled receptor-encoding deoxyribonucleic acid expressibly linked to a second promoter, wherein the G protein coupled receptor is capable of specifically activating the pheromone responsive pathway.

2. An isolated deoxyribonucleic acid sequence comprising an aequorin-encoding sequence expressibly linked to a promoter, wherein the promoter is responsive to activation by the pheromone responsive pathway and the promoter is made by a process comprising amplifying the promoter from wild-type yeast genomic DNA using two primers, one comprising SEQ ID NO: 6 and one comprising SEQ ID NO: 7.

3. The isolated deoxyribonucleic acid sequence of claim 2, further comprising a G protein coupled receptor-encoding deoxyribonucleic acid expressibly linked to a second promoter, wherein the G protein coupled receptor is capable of specifically activating the pheromone responsive pathway.

* * * * *

SEQUENCE LISTING

<160> NUMBER OF SEQ ID NOS: 7

<210> SEQ ID NO 1
<211> LENGTH: 591
<212> TYPE: DNA
<213> ORGANISM: Aequorea victoria
<220> FEATURE:
<221> NAME/KEY: CDS
<222> LOCATION: (1)..(591)
<223> OTHER INFORMATION:

<400> SEQUENCE: 1

```
atg aca agc aaa caa tac tca gtc aag ctt aca tca gac ttc gac aac      48
Met Thr Ser Lys Gln Tyr Ser Val Lys Leu Thr Ser Asp Phe Asp Asn
1               5                   10                  15 cca aga tgg att gga cga cac aag cat atg ttc aat ttc ctt gat gtc      96
Pro Arg Trp Ile Gly Arg His Lys His Met Phe Asn Phe Leu Asp Val
            20                  25                  30 aac cac aat gga aaa atc tct ctt gac gag atg gtc tac aag gca tct     144
Asn His Asn Gly Lys Ile Ser Leu Asp Glu Met Val Tyr Lys Ala Ser
        35                  40                  45 gat att gtc atc aat aac ctt gga gca aca cct gag caa gcc aaa cga     192
Asp Ile Val Ile Asn Asn Leu Gly Ala Thr Pro Glu Gln Ala Lys Arg
    50                  55                  60 cac aaa gat gct gta gaa gcc ttc ttc gga gga gct gga atg aaa tat     240
His Lys Asp Ala Val Glu Ala Phe Phe Gly Gly Ala Gly Met Lys Tyr
65                  70                  75                  80 ggt gtg gaa act gat tgg cct gca tat att gaa gga tgg aaa aaa ttg     288
Gly Val Glu Thr Asp Trp Pro Ala Tyr Ile Glu Gly Trp Lys Lys Leu
                85                  90                  95 gct act gat gaa ttg gag aaa tac gcc aaa aac gaa cca acg ctc atc     336
Ala Thr Asp Glu Leu Glu Lys Tyr Ala Lys Asn Glu Pro Thr Leu Ile
            100                 105                 110 cgt ata tgg ggt gat gct ttg ttt gat atc gtt gac aaa gat caa aat     384
Arg Ile Trp Gly Asp Ala Leu Phe Asp Ile Val Asp Lys Asp Gln Asn
        115                 120                 125 gga gcc att aca ctg gat gaa tgg aaa gca tac acc aaa gct gct ggt     432
Gly Ala Ile Thr Leu Asp Glu Trp Lys Ala Tyr Thr Lys Ala Ala Gly
    130                 135                 140 atc atc caa tca tca gaa gat tgc gag gaa aca ttc aga gtg tgc gat     480
Ile Ile Gln Ser Ser Glu Asp Cys Glu Glu Thr Phe Arg Val Cys Asp
145                 150                 155                 160 att gat gaa agt gga caa ctc gat gtt gat gag atg aca aga caa cat     528
Ile Asp Glu Ser Gly Gln Leu Asp Val Asp Glu Met Thr Arg Gln His
                165                 170                 175
```

```
tta gga ttt tgg tac acc atg gat cct gct tgc gaa aag ctc tac ggt    576
Leu Gly Phe Trp Tyr Thr Met Asp Pro Ala Cys Glu Lys Leu Tyr Gly
            180                 185                 190 gga gct gtc ccc taa                                                591
Gly Ala Val Pro
        195

<210> SEQ ID NO 2
<211> LENGTH: 196
<212> TYPE: PRT
<213> ORGANISM: Aequorea victoria

<400> SEQUENCE: 2

Met Thr Ser Lys Gln Tyr Ser Val Lys Leu Thr Ser Asp Phe Asp Asn
1               5                   10                  15

Pro Arg Trp Ile Gly Arg His Lys His Met Phe Asn Phe Leu Asp Val
            20                  25                  30

Asn His Asn Gly Lys Ile Ser Leu Asp Glu Met Val Tyr Lys Ala Ser
        35                  40                  45

Asp Ile Val Ile Asn Asn Leu Gly Ala Thr Pro Glu Gln Ala Lys Arg
    50                  55                  60

His Lys Asp Ala Val Glu Ala Phe Phe Gly Gly Ala Gly Met Lys Tyr
65                  70                  75                  80

Gly Val Glu Thr Asp Trp Pro Ala Tyr Ile Glu Gly Trp Lys Lys Leu
                85                  90                  95

Ala Thr Asp Glu Leu Glu Lys Tyr Ala Lys Asn Glu Pro Thr Leu Ile
            100                 105                 110

Arg Ile Trp Gly Asp Ala Leu Phe Asp Ile Val Asp Lys Asp Gln Asn
        115                 120                 125

Gly Ala Ile Thr Leu Asp Glu Trp Lys Ala Tyr Thr Lys Ala Ala Gly
    130                 135                 140

Ile Ile Gln Ser Ser Glu Asp Cys Glu Glu Thr Phe Arg Val Cys Asp
145                 150                 155                 160

Ile Asp Glu Ser Gly Gln Leu Asp Val Asp Glu Met Thr Arg Gln His
                165                 170                 175

Leu Gly Phe Trp Tyr Thr Met Asp Pro Ala Cys Glu Lys Leu Tyr Gly
            180                 185                 190

Gly Ala Val Pro
        195

<210> SEQ ID NO 3
<211> LENGTH: 278
<212> TYPE: DNA
<213> ORGANISM: Saccharomyces cerevisiae

<400> SEQUENCE: 3
aagcttggat cgcccttttt gacgtattga atggcataat tgcactgtca ctttcgcgc     60 tgtctcattt tggtgcgatg atgaaacaaa catgaaacgt ctgtaatttg aaacaaataa    120
cgtaattctc gggattggtt ttatttaaat gacaatgtaa gagtggcttt gtaaggtatg    180
tgttgctctt aaaatatttg gatacgacat cctttatctt ttttccttta agagcaggat    240
ataagccatc aagtttctga aaatcaccat gggaattc                            278

<210> SEQ ID NO 4
<211> LENGTH: 62
<212> TYPE: DNA
<213> ORGANISM: Artificial Sequence
<220> FEATURE:
```

-continued

```
<223> OTHER INFORMATION: PCR Primer

<400> SEQUENCE: 4
ccggaattcc ggatgacaag caaacaatac tcagtcaagc ttacatcaga cttcgacaac    60
cc                                                                  62

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
gggccttagg ggacagctcc accgtagagc                                    30

<210> SEQ ID NO 6
<211> LENGTH: 33
<212> TYPE: DNA
<213> ORGANISM: Artificial Sequence
<220> FEATURE:
<223> OTHER INFORMATION: PCR primer

<400> SEQUENCE: 6
ctaaagcttg gatcgccctt tttgacgtat tga                                33

<210> SEQ ID NO 7
<211> LENGTH: 37
<212> TYPE: DNA
<213> ORGANISM: Artificial Sequence
<220> FEATURE:
<223> OTHER INFORMATION: PCR Primer

<400> SEQUENCE: 7
agaattccca tggtgatttt cagaaacttg atggctt                            37
```